(12) United States Patent
Small et al.

(10) Patent No.: US 6,291,733 B1
(45) Date of Patent: Sep. 18, 2001

(54) PROCESS FOR DIMERIZING OLEFINS

(75) Inventors: Brooke L. Small; Eduardo J. Baralt, both of Kingwood; A. J. Marcucci, Houston, all of TX (US)

(73) Assignee: Chevron Chemical Company LLC, San Francisco, CA (US)

( * ) Notice: Subject to any disclaimer, the term of this patent is extended or adjusted under 35 U.S.C. 154(b) by 0 days.

(21) Appl. No.: 09/324,622

(22) Filed: Jun. 2, 1999

(51) Int. Cl.[7] .............................. C07C 2/26; C07C 2/34; C07C 2/24

(52) U.S. Cl. .................... 585/512; 585/510; 585/511; 585/513

(58) Field of Search .................... 585/510, 511, 585/512, 513

(56) References Cited

U.S. PATENT DOCUMENTS

| | | | | |
|---|---|---|---|---|
| 4,045,508 | * | 8/1977 | Cupples et al. | 260/683.15 B |
| 4,658,078 | * | 4/1987 | Slaugh et al. | 585/512 |
| 4,973,788 | * | 11/1990 | Lin et al. | 585/511 |
| 5,087,788 | * | 2/1992 | Wu | 585/512 |
| 5,420,373 | * | 5/1995 | Hope et al. | 585/525 |
| 5,550,307 | * | 8/1996 | Hope et al. | 585/525 |
| 5,625,105 | * | 4/1997 | Lin et al. | 585/511 |

FOREIGN PATENT DOCUMENTS

| | | |
|---|---|---|
| 1140821 | 1/1969 | (GB). |
| 1268555 | 11/1986 | (SU). |
| WO 99/02472 | * 1/1999 | (WO). |

OTHER PUBLICATIONS

Kretschmer, et al., Regioselective Homo– and Codimerization of a–Olefins Catalyzed by Bis(2,4,7–trimethylindenyl)yttrium Hydride, Organomettalics 1988, 17, pp. 284–286.*

Miller et al., Codimerization of a–Olefins and Conjugated Dienes by a Nickel–Based Coordination Catalyst, Jour. Amer. Chem. Soc., 89:15, Jul. 19, 1967, pp. 3756–3761.*

Heijden et al., A Zwitterionic Zirconocene Alkyl Complex as a Single–Component a–Olefin Dimerization Catalyst, Jour. Amer. Chem. Soc. 1998, 120, pp. 1112–1113.*

* cited by examiner

Primary Examiner—Walter D. Griffin
Assistant Examiner—Tam M. Nguyen
(74) Attorney, Agent, or Firm—W. Bradley Haymond; Reece A. Scott

(57) ABSTRACT

A method of dimerizing alpha-olefins to mostly linear internal olefin dimers using as a catalyst a transition metal complex with an activating co-catalyst.

32 Claims, 1 Drawing Sheet

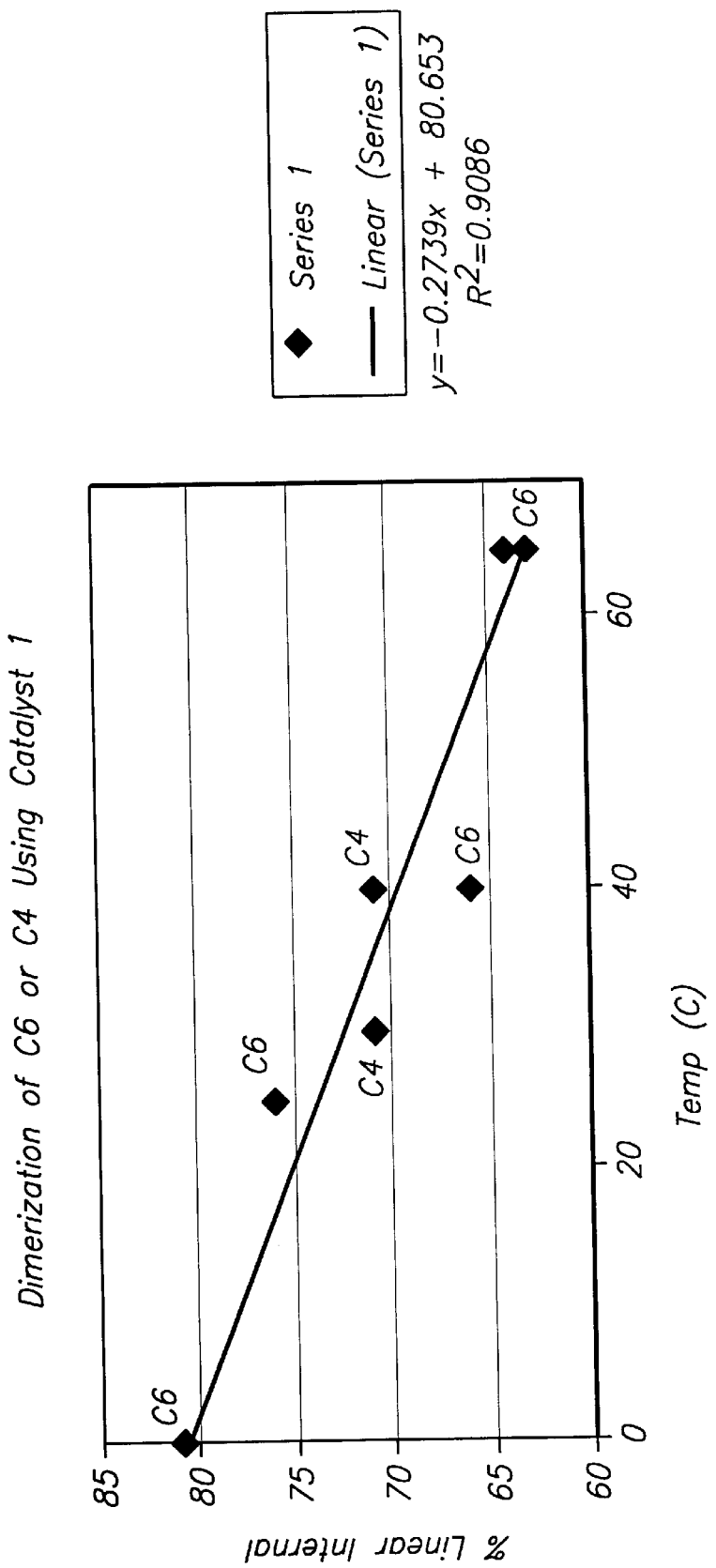

PROCESS FOR DIMERIZING OLEFINS

FIELD OF THE INVENTION

The present invention relates to the dimerization of alpha-olefins by catalyzing with a transition metal complex and a co-catalyst.

BACKGROUND OF THE INVENTION

Current alpha-olefin production processes yield large molar quantities of 1-butene, which has limited value. Thus, ways to avoid making 1-butene or to convert 1-butene into higher value products are desired. Catalysts have been used to dimerize 1-butene to octenes, but the selectivity of the catalysts for the more desired linear internal octene isomers is low, and the activity and conversion of the catalysts are low as well. A catalyst that is active and selective for dimerization is desired. The products may be used as precursors for production of plasticizers. Since 1-pentene, 1-hexene and 1-octene are also low molecular weight alpha olefins; they can also be dimerized for making linear internal olefin dimers.

Currently, vinylidenes can be produced using triisobutylaluminum to catalyze alpha olefin dimerization. In one embodiment, the reaction can use 0.5 weight percent triisobutylaluminum, take 4 to 6 hours, and be conducted at 170 to 220° C. Under these conditions, the reaction gives approximately 70 percent alpha olefin conversion. The converted product includes 80 to 90 weight percent vinylidene and 10 to 20 weight percent internal dimer olefins. Such a process is severely limited by high vinylidene olefin selectivity. Additional process disadvantages include a long reaction time and a high thermal requirement.

Alpha olefin dimerization technology to produce vinylidenes is known. In a preferred embodiment, the catalyst used in the technology is composed of bis(cyclopentadienyl)zirconium dichloride and an alumoxane in a molar ratio of 1:4 at a 1000:1 olefin:aluminum molar ratio at 40° C. Under these conditions, the reaction gives 93 percent alpha-olefin conversion in two hours. The converted product includes 95 weight percent dimer olefin and only 2 weight percent internal olefins. A disadvantage of this catalyst system is that it produces very little internal olefins. With proper catalyst selection, even under the most reasonable conditions, the internal olefin selectivity would still not make it economically feasible as a means of producing internal olefins.

The use of an alkylaluminum catalyst, 1 to 4 mole percent, at 100 to 140° C. has been disclosed. Specifically, the use of trioctylaluminum as the catalyst is disclosed. In a preferred embodiment of the patent, the catalyst concentration is 1.7 mole percent at 120° C. Under these conditions, the reaction gives a 90 percent alpha olefin conversion in 192 hours. The converted product includes 99 weight percent alpha olefin dimers, 95 weight percent vinylidene, and only 4 percent internal dimer olefins. Though the patent technology offers good dimer olefin selectivity, this patent does not represent an efficient manufacturing process due to the long reaction times and production of vinylidene olefins. Reaction times could be reduced by increasing the alkylaluminum catalyst concentration, increasing the reaction temperature, or reducing the conversion goal to less than 90 percent conversion. However, the reaction times would still be too long to provide a reasonable manufacturing process.

A catalyst system composed of bis(cyclopentadienyl)-zirconium dichloride, an aluminoxane other than methylaluminoxane (all examples use isobutylaluminoxane), and trimethylaluminum has also been disclosed. In a typical example, the catalyst system is approximately 7.5 mmoles aluminum (3.9 mmoles aluminoxane and 3.7 mmoles trimethylaluminum) and 0.11 mmoles of bis(cyclopentadienyl)zirconium dichloride and reacts with 128 mmoles of olefin at 50° C. Under these conditions, the catalyst gives a 92.7 percent alpha olefin conversion in six hours. The converted product includes 90 weight percent dimer vinylidene olefin and only 7 weight percent internal olefin. This system also has the disadvantage of producing vinylidene olefins and not enough internal olefins.

A method of manufacturing alpha-olefins by contacting ethylene with an iron complex of a selected 2,6-pyridinedicarboxaldehyde bisimine or a selected 2,6-diacylpyridine bisimine is also known. Although the catalysts used in this method are closely related to the catalysts used in the present invention, this method has not been connected with the dimerization of olefins. Rather, this method deals with the manufacture of alpha-olefins from ethylene.

In contrast, Applicants have achieved a process of dimerizing α-olefins using, as a pre-catalyst, a tridentate bisimine ligand coordinated to an iron center. This pre-catalyst is activated by the addition of a co-catalyst, which may be an alumoxane or a combination of a Lewis acid and an alkylating agent. Once activated, the catalyst dimerizes α-olefins rapidly to form a mixture of linear, internal olefin dimers and methyl-branched internal olefin dimers.

SUMMARY OF THE INVENTION

The invention relates to a method of making olefin dimers and method of using a transition metal complex to dimerize alpha-olefins comprising the steps of:

(a) Adding to a container under inert gas atmosphere a catalyst comprising a transition metal complex;

(b) Adding alpha-olefin monomer to the container with the catalyst;

(c) Adding to the container with the monomer and pre-catalyst an activating co-catalyst; and (d) Forming a linear internal olefin dimer mixture comprising linear internal olefin dimers and methyl-branched internal olefin dimers.

A preferred embodiment of the invention is a process for dimerizing at least 50 mole percent of an alpha-olefin monomer at a selectivity of at least 60 mole percent to linear internal olefin dimers. In a more preferred embodiment, at least 90 mole percent of the olefin dimer mixture is linear olefin or methyl-branched olefin.

BRIEF DESCRIPTION OF THE DRAWING

The FIGURE is a graph plotting the % linear internal olefin dimers vs. the temperature at which the reaction is run. Dimerization of both $C_6$ and $C_4$ is plotted using Catalyst 1.

DETAILED DESCRIPTION OF THE INVENTION

Alpha-olefins that can be used in the process include straight chain terminally unsaturated monoolefinic aliphatic hydrocarbons. Preferred alpha-olefins are those containing at least 4 and up to 36 or more carbon atoms. Most preferred alpha-olefins are 1-butene, 1-pentene and 1-hexene or a mixture of the group consisting of 1-butene, 1-pentene, 1-hexene and 1-octene.

Any transition metal complex with a co-catalyst may be used as a catalyst in the process. In a preferred embodiment, the activating co-catalyst may be alumoxane or a combination of a Lewis acid and an alkylating agent.

The preferred transition metal complexes are tridentate bisimine ligands coordinated to an iron center or a combination of an iron center and aryl rings, either substituted or unsubstituted.

The most preferred transition metal complexes are selected from the group consisting of catalysts 1, 2, 3, 4 and 5:

1

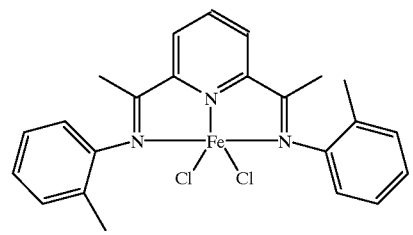

2

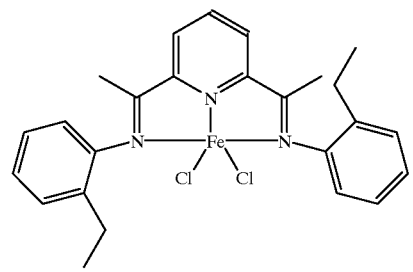

3

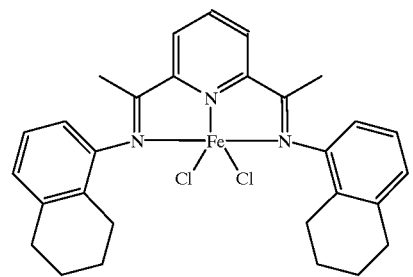

4

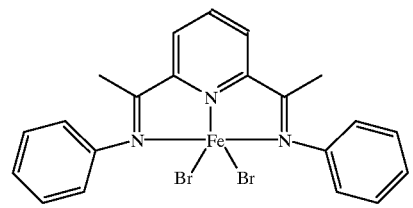

5

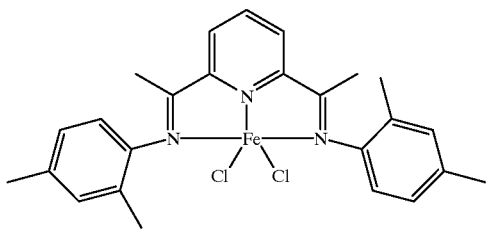

The effective amount of transition metal complex catalyst is quite low. With the catalyst and co-catalyst less than 1% by mass of the total alpha-olefin mixture, the dimerization reaction occurs in minutes.

A preferred catalyst concentration is 0.01–0.1 mg of catalyst per ml of alpha-olefin monomer. A more preferred catalyst concentration is 0.02–0.08 mg of catalyst per ml of alpha-olefin monomer. An even more preferred catalyst concentration is 0.05 to 0.06 mg of catalyst per ml of alpha-olefin monomer.

Preferred co-catalysts are selected from the group consisting of an alumoxane or a combination of a Lewis acid and an alkylating agent. A preferred co-catalyst is methylaluminumoxane (MMAO) in molar excess.

The following observations can be made about the reaction:

(1) The reaction proceeds more rapidly in neat α-olefin than in solution.

(2) The reaction initiated by addition of the co-catalyst can be conducted at a temperature in a range of from 0° C. to 85° C. The reaction proceeds more rapidly at elevated temperatures (30–70° C.). These temperatures are obtained by activating the reaction at room temperature and allowing the reaction exotherm to heat the solution.

(3) Conversion is limited by the decreasing concentration of substrate available. As the amount of dimer is increased, the concentration of α-olefin decreases. This may lead to catalyst deactivation.

There were two general procedures used for the dimerization experiments, with the difference depending on the nature of the substrate. For monomers that are liquids at standard atmospheric conditions, benchtop experiments were carried out using standard Schlenk line techniques to exclude excess moisture and air. For butene, the experiments were performed in a 500 ml Zipperclave reactor in liquid butene. The catalysts 1, 2, 3, 4 and 5 used are shown below.

1

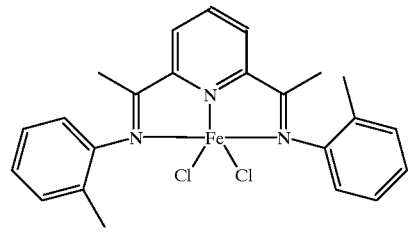

2

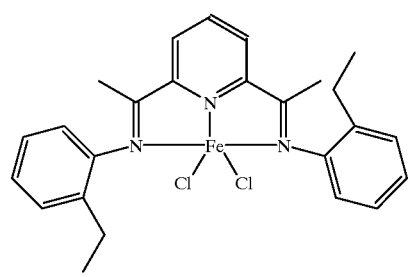

-continued

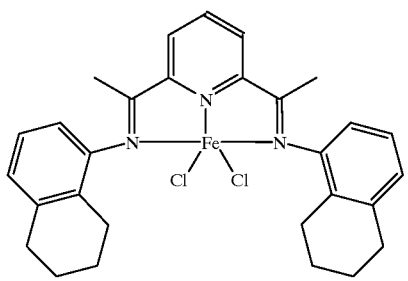

3

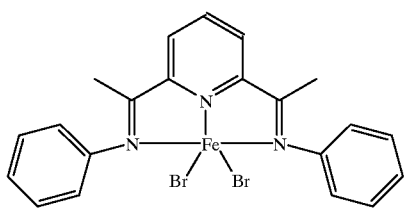

4

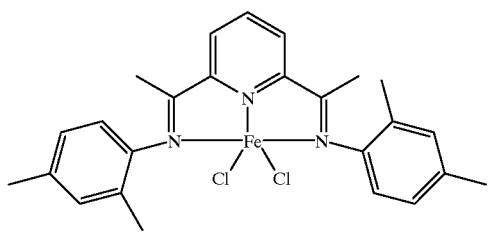

5

Dimerization Method 1

Dimerization of 1-hexene and Liquid Monomers

A two-necked flask with a stirbar was fitted with a reflux condenser on one neck and a thermocouple with the appropriate adapter on the other neck. The setup was heated under vacuum via the insertion of a needle in the septum at the top of the condenser. After heating, the setup was back-filled with nitrogen from the Schlenk manifold. The condenser was then removed under positive nitrogen flow and the pre-catalyst was added quickly. After replacing the condenser, the flask was back-filled three times with nitrogen and charged with the liquid monomer. In the cases of 1-hexene, the monomer was a commercial grade of Chevron Chemical's Gulftene-6. The monomer was used "as is". Stirring was begun in order to effectively slurry the sparingly soluble catalyst in the neat monomer. After several minutes, the co-catalyst was added via syringe. All of the reactions were activated at room temperature or lower, but the exothermic nature of the reaction caused the temperature in many cases to rise significantly. These temperatures were monitored using the thermocouple, and the temperatures listed in the table represent the maximum temperatures achieved in the reaction. In some cases, the exotherm was controlled by a water bath. After reaching the maximum temperature in each reaction, a cooling process was observed. This cooling does not necessarily indicate that the catalyst is becoming deactivated. It is quite likely a feature of the reaction kinetics, meaning that as the substrate is consumed, the heat of reaction per unit time begins to decrease accordingly. Examples 1 to 3, 5 to 8 and 10 to 18 of Table 1 were made using Dimerization Method 1.

Dimerization Method 2

Dimerization of 1-butene

A 500 ml Zipperclave reactor was heated under vacuum at 50° C. for several hours. The reactor was cooled to room temperature under nitrogen. The pre-catalyst was then quickly added to the reactor, and the reactor was resealed and placed under vacuum. A dual-chambered glass sample charger was then attached to the injection port of the reactor. From the first chamber, a small amount of cyclohexane (usually about 20 ml) was added. From the second chamber, more cyclohexane (usually about 10 ml) and the co-catalyst were added. The total amount of cyclohexane was carefully measured. The reactor was then quickly sealed and charged with 200 ml of liquid butene. The reactor was further pressurized with at least 100 psi of nitrogen to help keep the butene in the liquid phase. The reaction was stirred rapidly, and the temperature was monitored using a thermocouple. Exotherms due to the heat of reaction were observed, and the reaction temperatures listed correspond to the maximum temperatures observed in the reactions. Examples 4 and 9 of Table 1 were made using Dimerization Method 2.

Product Analysis Method

General Procedure for Analyzing Reaction Product

The aluminum co-catalysts were removed by pouring the liquid products into a water wash. After removal of the co-catalysts, the products were analyzed by gas chromatography (GC). GC analysis showed clear separation of the linear from the branched species, and hydrogenation of the products confirmed these results. The percentages of linear vs branched materials in the products were usually determined from the hydrogenation data, but it was often possible to determine these numbers accurately without hydrogenation. $^{13}C$ NMR and $^1H$ NMR were used to confirm the internal olefin content in the products, with only about 1% of vinylidene products present. The FIGURE is a plot constructed to show the selectivity for linear internal species for catalyst 1 with changes in temperature. Note that while the activity and the conversion of the catalyst decreases with decreasing temperature, the selectivity for internal olefins increases. Based on Example 13 in the Table 1, it appears that 40° C. may be the optimum temperature for running these reactions. Also, note from the plot that the selectivity for linear internal products does not depend on the monomer.

The conversions and yields were determined by comparing the product peaks to internal standard peaks, and by assuming equal response factors of the standards and the products. For the hexene dimerization experiments, 1-hexene was the internal standard, and for the butene experiments cyclohexane was used. The butene conversion levels are approximate because the exact density of butene under the reaction conditions is not known.

Table 1, below, collects the data from 18 experiments, fifteen experiments (Examples 1, 2, 3, 5, 6, 7, 8, 10, 11, 12, 13, 14, 15, 16 and 18) performed with the hexene monomer according to Dimerization Method 1, two experiments (Examples 4 and 9) performed with the butene monomer according to Dimerization Method 2, and one experiment (Example 17) performed with both pentene and hexene monomer according to Dimerization Method 1. Table 1 describes the various conditions used including which of the five catalysts were used.

TABLE 1

| Ex. | Catalyst | Loading (mg) | Co-catalyst | Loading | α-olefin monomer | Amount (ml) | React. length | React. temp. (° C.) | % conv. | Yield (g) | TON | % dimer | % linear internal | % methyl branched |
|---|---|---|---|---|---|---|---|---|---|---|---|---|---|---|
| 1 | 1 | 6.0 | MMAO, 6.42% Al | 2.0 ml | C6 | 20 | 10 min | ~65° C. | 55 | 7.4 | 6,800 | 92 | 64 | 35 |
| 2 | 1 | 1.0 | MMAO, 6.42% Al | 1.0 ml | C6 | 20 | 3 h | 25 | 21 | 2.8 | 15,600 | 92 | 76 | 23 |
| 3 | 1 | 1.0 | MMAO, 6.42% Al | 1.0 ml | C6 | 20 | 3 h | 0 | 9 | 1.2 | 6,700 | 85 | 81 | 18 |
| 4 | 1 | 5.1 | MMAO, 6.42% Al | 3.5 ml | C4 | 200 | 1 h | 30 | ~22 | 26.0 | 42,600 | 85 | 71 | 28 |
| 5 | 2 | 5.9 | MMAO, 6.42% Al | 3.0 ml | C6 | 50 | 1 h | ~30 | 28 | 9.4 | 9,400 | 87 | 71 | 28 |
| 6 | 1 | 11.7 | MMAO, 6.42% Al | 6.0 ml | C6 | 200 | 2 h | 65 | 29 | 39.3 | 18,700 | 85 | 63 | 36 |
| 7 | 3 | 5.8 | MMAO, 6.42% Al | 3.0 ml | C6 | 100 | 15 min | 53 | 26 | 17.6 | 19,400 | 90 | 70 | 29 |
| 8 | 4 | 10.7 | MMAO, 6.42% Al | 4.0 ml | C6 | 100 | 30 min | 82 | 58 | 39.2 | 23,100 | 96 | 27 | 70 |
| 9 | 1 | 10.0 | MMAO, 6.42% Al | 3.0 ml | C4 | 200 | 1 h | 40 | ~58 | 70.6 | 59,000 | 83 | 71 | 28 |
| 10 | 4 | 4.3 | MMAO, 6.68% Al | 3.0 ml | C6 | 100 | 2 h | 20 | 8 | 5.6 | 8,200 | 95 | 34 | 65 |
| 11 | 4 | 6.0 | MMAO, 6.68% Al | 3.0 ml | C6 | 100 | 1 h | 50 | 44 | 29.8 | 31,300 | 96 | 29 | 70 |
| 12 | 2 | 10.5 | MMAO, 6.68% Al | 3.0 ml | C6 | 100 | 4 h | 30 | 16 | 10.8 | 6,100 | 86 | 69 | 30 |
| 13 | 1 | 10.5 | MMAO, 6.68% Al | 6.0 ml | C6 | 200 | 5 h | 40 | 70 | 93.9 | 49,800 | 83 | 66 | 33 |
| 14 | 5 | 10.5 | MMAO, 6.68% Al | 6.0 ml | C6 | 200 | 1 h | 40 | 64 | 86.1 | 48,400 | 85 | 65 | 34 |
| 15 | 5 | 6.8 | MMAO, 6.68% Al | 3.0 ml | C6 | 100 | 2 h | 0 | 33 | 22.3 | 19,400 | 83 | 80 | 19 |
| 16 | 5 | 5.9 | MMAO, 6.68% Al | 3.0 ml | C6 | 100 | 1 h | 40 | 68 | 43.8 | 52,600 | 86 | 66 | 33 |
| 17[a] | 5 | 6.3 | MMAO, 6.68% Al | 3.0 ml | C5, C6 | 47, 53 | 1 h | 40 | 65 | 42.8 | 43,700 | 85 | 64 | 35 |
| 18 | 3 | 5.5 | MMAO, 6.68% Al | 3.0 ml | C6 | 100 | 1 h | 40 | 36 | 24.1 | 28,600 | 90 | 71 | 28 |

[a]Co-dimerization using 1-pentene and 1-hexene in equimolar amounts. GC analysis revealed that equimolar amounts (±5%) of each monomer were incorporated into the resultant dimers and trimers.

While the present invention has been described with reference to specific embodiments, this application is intended to cover various changes and those skilled in the art may make those substitutions without departing from the spirit and scope of the appended claims.

What is claimed is:

1. A method of making olefin dimers comprising the steps of:
    (a) adding to a container under inert gas a pre-catalyst comprising a transition metal complex comprising a transition metal complexed with a tridentate bisimine ligand bearing substituted or unsubstituted aryl rings;
    (b) adding alpha-olefin monomer to the container with the pre-catalyst;
    (c) adding to the container with the monomer and pre-catalyst an activating co-catalyst; and
    (d) forming an olefin dimer mixture comprising linear internal olefin dimers and methyl-branched internal olefin dimers.

2. The method of claim 1 wherein at least 50 mole percent of the alpha-olefin monomer is dimerized to internal olefin dimer.

3. The method of claim 1 wherein at least 90 mole percent of the olefin dimer mixture is linear olefin or methyl-branched olefin.

4. The method of claim 2 wherein at least 60 mole percent of the internal olefin dimer is linear internal olefin dimer.

5. The method of claim 1 wherein the transition metal is iron.

6. The method of claim 1 wherein the concentration of the pre-catalyst is in a range from 0.01 to 0.1 mg pre-catalyst per ml of alpha-olefin monomer.

7. The method of claim 6 wherein the concentration of the pre-catalyst is in a range from 0.02 to 0.08 mg pre-catalyst per ml of alpha-olefin monomer.

8. The method of claim 6 wherein the concentration of the pre-catalyst is in a range from 0.05 to 0.06 mg pre-catalyst per ml of alpha-olefin monomer.

9. The method of claim 1 wherein the pre-catalyst and activating co-catalyst are less than 1% by mass of the alpha-olefin monomer in the container.

10. The method of claim 1 wherein the activating co-catalyst is aluminumoxane or a combination of a Lewis acid and an alkylating agent.

11. The method of claim 5 wherein the transition metal complex is selected from the group consisting of structures 1, 2, 3, 4 and 5.

1

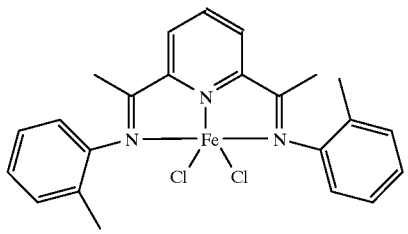

-continued

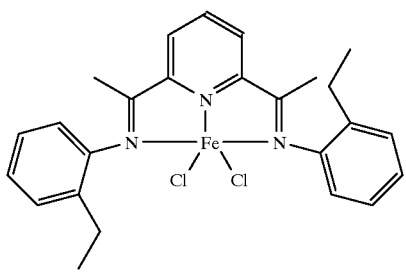

2

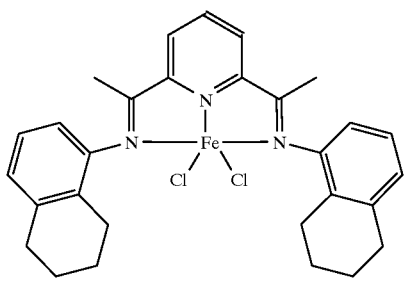

3

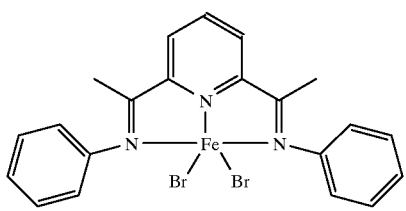

4

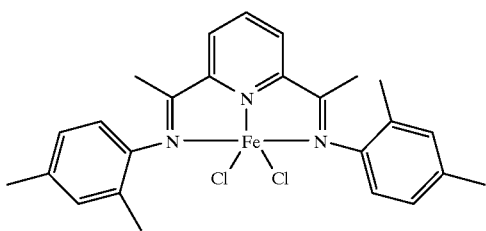

5

12. The method according to claim 1 wherein the alpha-olefin monomer is selected from the group consisting of normal alpha-olefin chains having from 4 to 36 carbon atoms.

13. The method according to claim 12 wherein the alpha-olefin monomer is selected from the group consisting of 1-butene, 1-pentene and 1-hexene.

14. The method according to claim 12 wherein the alpha-olefin monomer is a mixture of at least two of the group consisting of 1-butene, 1-pentene, 1-hexene and 1-octene.

15. The method according to claim 1 wherein the addition of activating co-catalyst in step (c) is conducted at a temperature in a range from 0° C. to 85° C.

16. The method according to claim 15 wherein the addition of activating co-catalyst in step c) is conducted at a temperature in a range from 30° C. to 85° C.

17. A method of using a pre-catalyst to dimerize alpha-olefins comprising the steps of:
(a) adding to a container under inert gas the pre-catalyst comprising a transition metal complex comprising a transition metal complexed with a tridentate bisimine ligand bearing substituted or unsubstituted aryl rings;
(b) adding alpha-olefin monomer to the container with the pre-catalyst;
(c) adding to the container with the monomer and pre-catalyst an activating co-catalyst; and
(d) forming an olefin dimer mixture comprising linear internal olefin dimers and methyl-branched internal olefin dimers.

18. The method of claim 17 wherein at least 50 mole percent of the alpha-olefin monomer is dimerized to internal olefin dimer.

19. The method of claim 17 wherein at least 90 mole percent of the olefin dimer mixture is linear olefin or methyl-branched olefin.

20. The method of claim 18 wherein at least 60 mole percent of the internal olefin dimer is linear internal olefin dimer.

21. The method of claim 17 wherein the transition metal is iron.

22. The method of claim 17 wherein the concentration of the pre-catalyst is in a range from 0.01 to 0.1 mg pre-catalyst per ml of alpha-olefin monomer.

23. The method of claim 22 wherein the concentration of the pre-catalyst is in a range from 0.02 to 0.08 mg pre-catalyst per ml of alpha-olefin monomer.

24. The method of claim 22 wherein the concentration of the pre-catalyst is in a range from 0.05 to 0.06 mg pre-catalyst per ml of alpha-olefin monomer.

25. The method of claim 17 wherein the pre-catalyst and activating co-catalyst are less than 1% by mass of the alpha-olefin monomer in the container.

26. The method of claim 17 wherein the activating co-catalyst is aluminumoxane or a combination of a Lewis acid and an alkylating agent.

27. The method of claim 22 wherein the transition metal complex is selected from the group consisting of structures 1, 2, 3, 4 and 5:

1

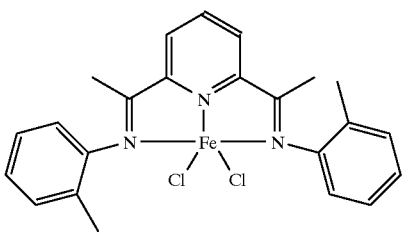

2

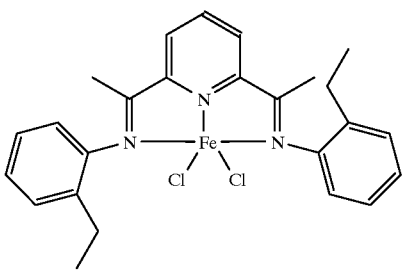

3

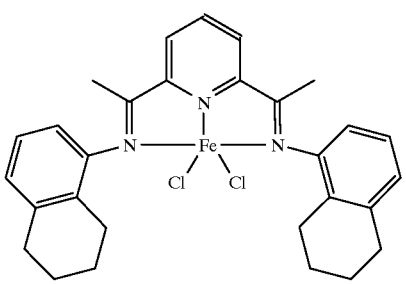

-continued

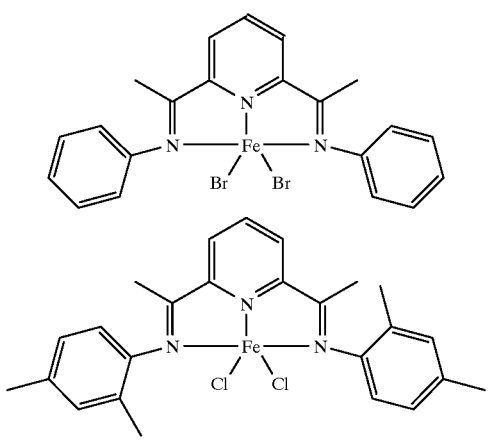

28. The method according to claim 17 wherein the alpha-olefin monomer is selected from the group consisting of normal alpha-olefin chains having from 4 to 36 carbon atoms.

29. The method according to claim 28 wherein the alpha-olefin monomer is selected from the group consisting of 1-butene, 1-pentene and 1-hexene.

30. The method according to claim 28 wherein the alpha-olefin monomer is a mixture of at least two of the group consisting of 1-butene, 1-pentene, 1-hexene and 1-octene.

31. The method according to claim 17 wherein the addition of activating co-catalyst in step (c) is conducted at a temperature in a range from 0° C. to 85° C.

32. The method according to claim 31 wherein the addition of activating co-catalyst in step (c) is conducted at a temperature in a range from 30° C. to 85° C.

* * * * *